(12) United States Patent
Shuman (10) Patent No.: US 10,350,383 B2
(45) Date of Patent: Jul. 16, 2019

(54) VARIABLE STIFFNESS MEDICAL DEVICE

(71) Applicant: Spiration, INC., Redmond, WA (US)

(72) Inventor: Brandon Shuman, Kirkland, WA (US)

(73) Assignee: Spiration, INC., Redmond, WA (US)

( * ) Notice: Subject to any disclaimer, the term of this patent is extended or adjusted under 35 U.S.C. 154(b) by 11 days.

(21) Appl. No.: 15/558,323

(22) PCT Filed: Feb. 26, 2016

(86) PCT No.: PCT/US2016/019682
§ 371 (c)(1),
(2) Date: Sep. 14, 2017

(87) PCT Pub. No.: WO2016/153719
PCT Pub. Date: Sep. 29, 2016

(65) Prior Publication Data
US 2018/0064908 A1 Mar. 8, 2018

Related U.S. Application Data

(60) Provisional application No. 62/138,724, filed on Mar. 26, 2015.

(51) Int. Cl.
*A61M 25/00* (2006.01)
*A61B 17/34* (2006.01)
(Continued)

(52) U.S. Cl.
CPC ..... *A61M 25/0054* (2013.01); *A61B 1/00078* (2013.01); *A61B 17/3478* (2013.01);
(Continued)

(58) Field of Classification Search
CPC ............ A61M 25/0054; A61M 25/005; A61M 2025/0175; A61M 2025/0004;
(Continued)

(56) References Cited

U.S. PATENT DOCUMENTS 5,797,882 A    8/1998   Purdy et al.
6,685,679 B2 *   2/2004   Merdan ............. A61M 25/0043
                                                        604/264
(Continued)

FOREIGN PATENT DOCUMENTS

| EP | 0824932 A2 | 2/1998 |
| JP | 2009-540919 A | 11/2009 |
| WO | 2004/030740 A1 | 4/2004 |

OTHER PUBLICATIONS

International Search Report and Written Opinion for International Application No. PCT/US2016/019682, dated Jun. 28, 2016.
Japanese Office Action for Japanese Patent Application No. 2017-550123; dated Jun. 28, 2018.

*Primary Examiner* — Theodore J Stigell
(74) *Attorney, Agent, or Firm* — The Dobrusin Law Firm, P.C.

(57) ABSTRACT

A device including a catheter (14) and a medical instrument (12). The catheter includes an inner portion (16) and one or more unlocking features (18). The medical instrument includes one or more locking features (24). When the medical instrument is in the inner portion of the catheter, the one or more unlocking features engage the one or more locking features so that the medical instrument can bend in the catheter. When the medical instrument is outside the catheter, the one or more unlocking features disengage from the one or more locking features so that the medical instrument is restricted from bending.

20 Claims, 3 Drawing Sheets

(51) Int. Cl.
*A61B 1/00* (2006.01)
*A61B 17/00* (2006.01)
*A61M 25/01* (2006.01)
*A61M 25/09* (2006.01)

(52) U.S. Cl.
CPC ...... *A61M 25/005* (2013.01); *A61M 25/0023* (2013.01); *A61M 25/0084* (2013.01); *A61B 1/00154* (2013.01); *A61B 2017/003* (2013.01); *A61M 2025/0004* (2013.01); *A61M 2025/0175* (2013.01); *A61M 2025/0915* (2013.01)

(58) Field of Classification Search
CPC .......... A61M 25/0023; A61M 25/0084; A61B 1/00078; A61B 1/00154; A61B 17/3478; A61B 2017/003
See application file for complete search history.

(56) References Cited

U.S. PATENT DOCUMENTS

| | | | |
|---|---|---|---|
| 6,855,124 B1 | 2/2005 | Gonzalez et al. | |
| 7,947,000 B2* | 5/2011 | Vargas | A61M 25/0021 600/587 |
| 2005/0080400 A1* | 4/2005 | Corcoran | A61B 17/0057 604/523 |
| 2010/0256740 A1 | 10/2010 | Limom et al. | |
| 2011/0218529 A1* | 9/2011 | Garcia | A61B 18/18 606/41 |
| 2014/0276051 A1 | 9/2014 | Hoffman | |
| 2016/0271366 A1* | 9/2016 | Quearry | A61M 25/0026 |

* cited by examiner

VARIABLE STIFFNESS MEDICAL DEVICE

FIELD

The present teachings relate to a medical device, and more particularly to a medical device that is generally flexible in one configuration and generally rigid in another configuration.

BACKGROUND

In certain medical procedures, a generally flexible medical device or needle may be preferred over a generally rigid medical device or needle. For example, a generally flexible needle may be preferred during needle insertion and needle steering in the anatomy. In other medical procedures, however, a generally stiff or rigid needle may be preferred. Some medical procedures may require a surgeon to use a generally flexible needle and a generally rigid or stiff needle. For example, during a tissue sampling procedure, a surgeon may be required to insert and steer a generally flexible needle and catheter through the anatomy, remove the flexible needle form the catheter and the anatomy, and then insert a generally rigid needle into the catheter and the anatomy to perform the tissue sampling function at a site of interest. Accordingly, such a procedure may be cumbersome for the surgeon, time consuming, and may cause unnecessary trauma to the patient.

It may therefore be desirable to have a variable stiffness medical device. That is, it may be desirable to have a medical device that is generally flexible in one configuration or during certain portions of a medical procedure and generally rigid or stiff in another configuration or during other portions of a medical procedure. It may be desirable to have a medical instrument such as a needle that is generally flexible when located within a catheter and generally rigid when located outside of the catheter. It may be attractive to provide a variable stiffness medical device that can be mass-produced relatively inexpensively, that has a minimal number of parts, and that is easy to operate.

SUMMARY

The present teachings meet one or more of these needs by providing a variable stiffness medical device. The present teachings provide a medical device that is generally flexible in one configuration or during certain portions of a medical procedure and generally rigid or stiff in another configuration or during other portions of a medical procedure. The present teachings provide a medical device, which comprises a catheter and a medical instrument moveably supported in the catheter. The catheter includes one or more unlocking features. The medical instrument includes one or more locking features. When the medical instrument is inserted into an inner portion of the catheter, the one or more unlocking features engage or unlock the one or more locking features so that the medical instrument is generally flexible. When the medical instrument is outside of the catheter, the one or more unlocking features disengage from the one or more locking features or lock the one or more locking features so that the medical instrument is generally rigid. The present teachings provide a single medical device that can be used for various medical procedures that may require both a generally rigid or stiff device and a generally flexible device. The present teachings provide a variable stiffness medical device that can be mass-produced relatively inexpensively, that has a minimal number of parts, and that is easy to operate.

The present teachings provide a device comprising a catheter and a medical instrument. The catheter includes an inner portion and one or more unlocking features. The medical instrument includes one or more locking features. When the medical instrument is in the inner portion of the catheter, the one or more unlocking features engage or unlock the one or more locking features so that the medical instrument can bend in the catheter. When the medical instrument is outside of the catheter, the one or more unlocking features disengage from the one or more locking features or lock the one or more locking features so that the medical instrument is restricted from bending.

The present teachings further provide a method comprising inserting a medical instrument, for example a needle, into the catheter; engaging the locking features of the medical instrument with the unlocking features of the catheter so that the medical instrument can bend and articulate in the catheter, and inserting the medical instrument and the catheter into the anatomy. The catheter includes an inner portion and one or more unlocking features. The medical instrument includes one or more locking features.

DETAILED DESCRIPTION

This Application claims priority to U.S. Provisional Application No. 62/138,724, filed on Mar. 26, 2015, the entirety of which is hereby incorporated by reference herein for all purposes. The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the description herein, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description. The teachings herein may be used without limitation. In other words, the teachings herein may be used in any medical procedure. The teachings herein may be used for accessing any part of any anatomy. For example, one or more, or various vessels, passages, lumens, body cavities, tissue, organs, the like, or a combination thereof in humans and animals can be accessed using the teachings herein.

The teachings include one or more medical devices. The one or more medical devices may comprise a catheter and any medical instrument. The catheter may include an inner portion and one or more unlocking features. The medical instrument may include one or more locking features. Generally, when the medical instrument is inserted or received in the inner portion of the catheter, the one or more unlocking features may engage or unlock the one or more locking features so that the medical instrument can bend and is generally flexible in the catheter. When the medical instrument is outside of the catheter, the one or more unlocking features may disengage from the one or more locking features or cause the one or more locking features to lock so that the medical instrument may be restricted from bending and may be generally rigid and stiff.

The one or more medical devices may function to be used in any medical procedure or obtain any material(s) or object(s) from the anatomy. For example, the one or more medical devices may function to introduce into any anatomy any medical instrument and/or facilitate the removal from any anatomy any medical instrument or materials. Exemplary medical instruments may include one or more needles, coring needles, sampling needles, transbronchial needle aspiration devices, cytology brushes, biopsy forceps, baskets, balloons, guiding devices, ultrasonic probes, illumination devices, energy devices, medicines, therapies (i.e., chemotherapy, proteinomics, microspheres, etc.), materials (i.e., liquids, pastes, markers, etc.), the like, or a combination thereof may be introduced into the anatomy and/or removed therefrom. In some embodiments the medical device may include one or more needles, for example one or more coring needles, sampling needles, and transbronchial needle aspiration devices. Exemplary material the medical devices may obtain from the body include, tissue samples, blood samples, abnormalities, foreign matter, and/or any other type of sample may be obtained from the anatomy via the one or more medical devices.

The one or more devices may include one or more catheters. The one or more catheters may function to provide for introduction into any anatomy and/or removal therefrom any medical instrument. In some embodiments, the one or more catheters may function to receive and engage the one or more medical instruments so that the one or more medical instruments can bend, articulate, and can be generally flexible therein. In other words, in one configuration, once the one or more medical instruments are at least partially received in the one or more catheters, the received portions of the one or more medical instrument may be at least partially or generally flexible, bendable, articulable, or a combination thereof so that access to regions of interest in the anatomy can be easily navigated. Once engaged or unlocked, the one or more catheters and the engaged or unlocked portions of the one or more medical instruments may be flexible, and may bend, articulate, and have low column strength. The disengaged or locked portions of the one or more medical instruments (i.e., some or all of the portions of the one or more medical instruments that are not received in and engaged by the one or more catheters) may be generally rigid, stiff, and may have high column strength.

The one or more catheters may be fabricated from any material suitable for use in any medical procedure. For example, the one or more catheters may be fabricated from a material that can be inserted into the anatomy while also performing the previously recited functions. The one or more catheters may be at least partially resilient, expandable, collapsible, formable, deformable, or a combination thereof. The one or more catheters may be one or more tubular members. The one or more catheters may be an elongated member extending along any axis, like a longitudinal axis, a catheter axis, a medical instrument axis, or a combination thereof. The one or more catheters may include any cross section suitable for performing the previously recited functions. For example, the cross section may be substantially circular, oval, or irregular. Along a length of the one or more catheters, the cross section may be uniform, or may vary, taper, widen, narrow, or a combination thereof. The one or more catheters may include or define an aperture or opening at a distal end, a proximal end, and/or at a region in between so that any medical instrument(s), medicine(s), object(s), or a combination thereof can pass there through and/or extend there out.

The one or more catheters may include one or more unlocking features. The one or more unlocking features may function to engage any medical instrument, any locking device of any medical instrument, or both received in the one or more catheters so that the medical instrument and/or the engaged or unlocked portions of the medical instrument can flex, bend, articulate, and have low column strength. Once at least a portion of the medical instrument is removed from the catheter, the one or more unlocking features may function to disengage from the one or more medical instruments, locking features of the one or more medical instruments, or both so that the medical instrument and/or the disengaged portions of the medical instrument are generally rigid, stiff, straight, and have high column strength. The one or more unlocking features may be any feature(s) that performs these recited functions. For example, the one or more unlocking features may be an inner surface or the inner diameter of the one or more catheters; may be any feature integrally formed with the inner surface or the inner diameter of the catheter; and/or may be any feature connected to the inner surface or inner diameter of the catheter. The one or more unlocking features may be one or more pins, nubs, dimples, raised portions, surfaces, ribs, members, extensions, projections, fingers, ridges, thickened portions, or a combination thereof. In some embodiments, the one or more unlocking features may be one or more ribs, or preferably, two or more ribs extending along at least a portion of the length of an inner surface of the one or more catheters. The one or more unlocking features may be two or more ribs that are equally spaced about an inner surface of the one or more catheters. The one or more unlocking features may extend along any axis, such as a longitudinal axis, a catheter axis, a needle axis, or a combination thereof. Along a length of the one or more catheters, the one or more unlocking features may have a uniform height, or the height may vary, change, taper, or a combination thereof. The one or more unlocking features may be continuous, or may extend in one or more sections along a length of the inner surface of the one or more catheters, around an inner diameter of the one or more catheters, or a combination thereof. The one or more unlocking features may be at least partially deformable, flexible, articulable, bendable, or a combination thereof. The one or more unlocking features may generally conform to, and may be moveably supported within one or more corresponding unlocking feature reliefs on the one or more medical instruments. The one or more unlocking features may have edges or sides that are generally straight, sloped, angled, rounded, or a combination thereof. The one or more unlocking features may have a uniform width, or the width may vary, change, taper, or a combination thereof. The one or more unlocking features may be helically wrapped along or around an inner surface or portion of the one or more catheters. The one or more unlocking features may be fabricated from any material suitable for use in medical procedure. For example, the one or more unlocking features may be fabricated from a material that can be inserted into the body and can also perform the functions recited above. Preferably, the one or more unlocking features may be fabricated from the same material as the one or more catheters. Engaging and disengaging the one or more medical instruments or the one or more locking features of the one or more medical instruments with the one or more unlocking features may comprise any method, step or action that achieves the functions recited above and is in essence contacting the unlocking feature with the locking feature so as to disengage the locking feature and allow the medical device to flex, bend, articulate, and have low column strength. For example, engaging may be contacting, depressing, biasing, moving, translating, pressing, pushing, compressing, deforming, bending, flexing, breaking, the like, and/or a combination thereof the one or more medical instruments and/or the locking features. Disengaging, for example, may be releasing, biasing, moving, flexing, translating, pushing, bending, the like, and/or a combination thereof the one or more medical instruments and/or locking features.

The one or more medical instruments may be any medical instrument that may function to be used in any medical procedure. The one or more medical instruments may be any medical instrument that may be inserted into the one or more catheters. The one or more medical instruments may be any instrument(s) for delivering medicine or therapy to the anatomy, or may be used for obtaining any material(s), sample(s), and/or object(s) from the anatomy. The one or more medical instruments may be one or more needles, cytology brushes, biopsy forceps, baskets, balloons, guiding devices, ultrasonic probes, illumination devices, energy devices, the like or a combination thereof. Preferably, the one or more medical instruments may be any needle(s). For example, the one or more needles may be a coring needle, a sampling needle, a transbronchial aspiration needle, a puncturing needle, a guiding needle, the like, or a combination thereof.

The one or more medical instruments may include one or more flexibility reliefs. The one or more flexibility reliefs may function to allow the one or more medical instruments to flex, bend, articulate, and have low column strength. The one or more flexibility reliefs may be any feature(s) that may function to provide the above-recited function. For example, the one or more flexibility reliefs may be one or more reliefs, cuts, depressions, thinned-out portions, notches, grooves, cutouts, apertures, openings, orifices, holes, recesses, the like or a combination thereof. The one or more flexibility reliefs may extend along an entire length of the one or more medical instruments, or along a selected portion thereof. The one or more flexibility reliefs may extend at least partially around a circumference of an outer portion of the one or more medical instruments. The one or more flexibility reliefs may extend in one or more sections. Preferably, the one or more flexibility reliefs may extend in two or more opposing segments relative to a longitudinal axis of the one or more medical instrument (i.e., one flexibility relief segment located at about 0 degrees relative to a center axis and another located at about 180 degrees). The one or more flexibility reliefs may extend in three or more, four or more, or even five or more segments that are equally spaced or irregularly spaced relative to a central axis extending along a length of the one or more medical instruments.

The one or more medical instruments may include one or more locking features. When the one or more medical instruments are inserted or received into the one or more catheters, the one or more locking features may be engaged or unlocked by the one or more unlocking features so that the one or more medical instruments can flex, bend, articulate, and have low column strength. The one or more locking features may function to restrict or prevent portions of the one or more medical instruments from flexing, bending, moving, articulating, or a combination thereof when the one or more locking features are not within the one or more catheters and are not engaged (i.e. are disengaged) by the one or more unlocking features. That is, the locking features may be resilient so that when not engaged or are disengaged by the unlocking features, the locking features lock and prevent flexing, bending, moving, articulating of the medical instrument. The one or more locking features may function to restrict or prevent the one or more medical instruments from bending or flexing about the one or more flexibility reliefs when the one or more medical instruments are not within the one or more catheters; when the one or more locking features are not engaged by the one or more unlocking features of the one or more catheters, or both. The one or more locking features may be any feature(s) that may perform the above-recited functions. For example, the one or more locking features may be one or more locking tabs, one or more hinges, or both.

The one or more locking tabs may be one or more pins, ribs, members, extensions, projections, fingers, ridges, the like, or a combination thereof. Preferably, the one or more locking tabs may be fabricated from the same material as the one or more medical instruments. The one or more locking tabs may be integrally formed with the one or more medical instruments, or may be mechanically attached thereto. The one or more locking tabs may be at least partially rigid. The one or more locking tabs, or one or more portions of the one or more locking tabs may be at least partially deformable, flexible, articulable, bendable, or a combination thereof. The one or more locking tabs may be located in an inner portion of the one or more medical instruments, an outer portion, or both. The one or more locking tabs may extend along any axis, such as a longitudinal axis, a catheter axis, a medical instrument axis, or a combination thereof. The one or more locking tabs may be irregularly or non-equally spaced around an inner portion of the one or more medical instruments. The one or more locking tabs may be generally perpendicular, or may be angularly oriented, relative to a longitudinal axis, a catheter axis, a medical instrument axis, or a combination thereof. The one or more locking tabs may extend in segments or groups along an entire length of the one or more medical instruments, or along a selected portion thereof. Preferably, the one or more locking tabs may be disposed in two segments along a length of the one or more medical instruments, with one segment located at about 0 degrees relative to a center axis and another located at about 180 degrees relative to the central axis. Each of the one or more locking tabs may cantilever from an inner portion of the one or more medical instruments. That is, the one or more locking tabs may have one end that is fixedly connected to an inner portion of the one or more medical instruments and one end that is moveable from an inner portion of the one or more medical instruments. In a steady state or locked position, a free end of the one or more locking tabs may engage or be resiliently biased against the inner portion of the one or more medical instruments so that the medical instrument is restricted from bending, moving, articulating, flexing, or a combination thereof. Portions of the one or more medical instruments may be in a steady state or locked position when located or positioned outside of the one or more catheters. In a biased or unlocked position, one or more locking tabs, or ends of the one or more locking tabs may be disengaged or separated from the inner portion of the one or more medical instruments so that the medical instruments can bend, move, articulate, flex, or a combination thereof at the flexibility reliefs. Portions of the one or more medical instruments may be in a biased or unlocked position when located inside of the one or more catheters. The one or more unlocking features may move, flex, bias, and/or engage the one or more locking tabs into the unlocked position so that corresponding portions of the needle can move, bend, flex, articulate, or a combination thereof.

The one or more hinges may be one or more thinned portions (often referred to as living hinge, for example), mechanical hinges, flexible portions, lowered portions, or a combination thereof. The one or more hinges may be integrally formed with the one or more medical instruments, or may be mechanically attached thereto. The one or more hinges may be at least partially deformable, flexible, articulable, bendable, or a combination thereof. The one or more hinges may be fabricated from a flexible material. The one or more hinges may be disengaged (i.e. locked position) by removing the one or more medical instruments from an inner portion or area of the catheter so that the one or more medical instruments can flex, bend, articulate, or a combination thereof. In the disengaged or locked position, the one or more medical instruments may have an oval cross section and may be restricted from bending, flexing, articulating, or a combination thereof. The one or more hinges may be engaged (i.e., unlocked position) by inserting the one or more medical instruments into an inner portion or area of the catheter so that the unlocking features can engage the hinge(s) so that the one or more medical instruments can flex, bend, articulate, or a combination thereof. In the engaged or unlocked position, the unlocking features of the catheter may flex, bias, or move the medical instruments from an oval cross section to a generally circular cross section.

The one or more hinges may include one or more interlocking extensions and one or more interlocking recesses. The one or more interlocking extensions may cooperate with the one or more interlocking recesses to create the one or more hinges. Each of the one or more interlocking extensions may fit into a correspondingly shaped interlocking recess in the locked position. The one or more interlocking extensions may have any shape corresponding to an interlocking recess, which may also have any corresponding shape for performing the aforementioned functions of the locking features. Preferably, the one or more interlocking extensions have a circular shape preferably corresponding to a circular interlocking recess. Preferably, the one or more interlocking extensions may have a triangular shape corresponding to a triangular interlocking recess. The one or more interlocking extensions, the one or more interlocking recesses, or both may be flexed, displaced, moved, compressed, depressed, engaged, biased, or a combination thereof by the unlocking features when a corresponding portion of the one or more medical instruments is located in the one or more catheters. The hinge may become flexible because there are limited points of contact when compressed and the hinge is opened (i.e. inside the sheath). The lack of many points of contact (or holes in the tube) allow for bending and flexibility. In its natural position, when the hinge is closed, (when the catheter or sheath are not forcing it more circular), the hinges snap into a configuration where there are many more points of contact, making it more like a rigid tube.

The one or more medical instruments may include one or more unlocking feature reliefs. The one or more unlocking feature reliefs may function to receive and engage the one or more unlocking features of the one or more catheters when the one or more medical instruments are received in the one or more catheters. The one or more unlocking feature reliefs may function to prevent the one or more medical instruments from rotating within the one or more catheters; may function to provide an area for the one or more locking features; and allow the one or more medical instruments to flex, bend, articulate, or a combination thereof when in the unlocked position, or a combination thereof. The one or more unlocking feature reliefs may be any feature(s) that may perform the aforementioned functions. For example, the one or more unlocking feature reliefs may be one or more grooves, channels, notches, openings, passages, troughs, or a combination thereof. The one or more unlocking feature reliefs may extend along an entire length of the one or more medical instruments, or may extend in one or more segments or portions.

The one or more medical instruments may be one or more needles. The one or more needles that may be inserted into the one or more catheters so that the one or more needles can be generally flexible. That is, the one or more needles may be inserted into the one or more catheters so that the one or more unlocking features can engage the one or more locking features of the needle so that the engaged portions are generally flexible. The one or more needles may function to be removed from the one or more catheters so that the one or more needles can be generally rigid and stiff. That is, the one or more needles may be removed from the one or more catheters so that the one or more unlocking features can disengage from the one or more locking features of the needle so that the engaged portions are generally rigid and stiff and restricted from bending.

The one or more needles may have any length that is suitable for use in any medical procedure. The length of the one or more needles may extend along any axis, such as a longitudinal axis, a needle axis, a catheter axis, or a combination thereof. The one or more needles may have any cross section that is suitable for use in any medical procedure. For example, the cross section of the one or more needles may be constant, may vary, may taper, may be irregular, may be any shape, or a combination thereof. For example, the cross section of the one or more needles may be generally circular, oval, irregular, or any other suitable shape to perform the above recited functions. The cross section of the one or more needles may be generally oval in a steady state condition when the one or more needles are not received in the one or more catheters. In a steady state condition, the one or more needles may be generally rigid and stiff. Once received in the one or more catheters, the generally oval cross section of the one or more needles may be engaged by the one or more unlocking features so that the cross section is generally circular and the one or more needles are generally flexible.

The one or more needles may be generally hollow. The one or more needles may be generally solid. The one or more needles may include one or more sections or portions that are generally solid, generally hollow, or both. The one or more needles may be formed from any material suitable for use in any medical procedure. For example, the one or more needles may be fabricated from a material that can be inserted into the anatomy, while still being able to bend, flex and/or articulate when engaged by the one or more unlocking features of the catheters and be generally rigid and stiff when disengaged by the one or more unlocking features. The one or more needles may be constructed from one or more hypotubes. The one or more needles may be constructed from one or more hypotubes that are relatively smooth and able to freely slide, rotate, or otherwise move within the catheter and/or the anatomy. The one or more needles may be any size or gauge suitable for use in any medical procedure, while still functioning to perform the above recited functions. For example, the one or more needles may be about 25 gauge or more, about 22 gauge, about 21 gauge, or about 19 gauge or less, etc. The one or more needles may include a combination of two or more gauges. That is, for example, a proximal portion of the needle may be about 21 gauge and a distal portion of the needle may be about 19 gauge, or vice versa. The one or more needles may comprise two or more needle portions that are joined together fixedly, permanently, temporarily, or a combination thereof. The two or more needle portions may be the same gauge, or may be different gauges. The one or more needles may be made from a single integral portion, or preferably, the one or more needles can be made from two or more portions or halves. The two or more portions or halves can be laser cut. For example, a first portion or half and first locking features can be laser cut, and a corresponding second portion or half can also be laser cut. Both portions or halves can then be joined together using one or more mechanical fasteners (i.e., welding, bonding, guiding, etc.).

The one or more needles may include one or more holes, ports, slots, the like or a combination thereof for tissue sample collection; for introducing one or more devices into the needle; for introducing one or more devices into the anatomy; for introducing medicine or therapy to the anatomy; or a combination thereof. The one or more needles may be advanced towards and/or retracted from the region of interest via the one or more catheters.

The medical device, the catheter, the medical instrument, or a combination thereof may be used with a method. The method steps may be performed in virtually any order. The method steps may include inserting the medical instrument or needle into the catheter; engaging one or more of the locking features of the medical instrument or needle with the unlocking features of the catheter so that the needle can bend and articulate in the catheter; and inserting the instrument or needle and the catheter into the anatomy. The method may include the steps of moving at least a first portion of the medical instrument or needle out of the catheter so that the locking features located at the first portion of the medical instrument or needle are disengaged by the unlocking features of the catheter and engaging one or more locking tabs of the locking features with one or more projections of the unlocking features so that the medical instrument or needle can bend and articulate in the catheter. The method may also include a step of engaging one or more hinges of the locking features with the inner portion of the catheter so that the medical instrument or needle can bend and articulate in the catheter. The catheter includes an inner portion and one or more unlocking features. The needle includes one or more locking features.

Figure 1:
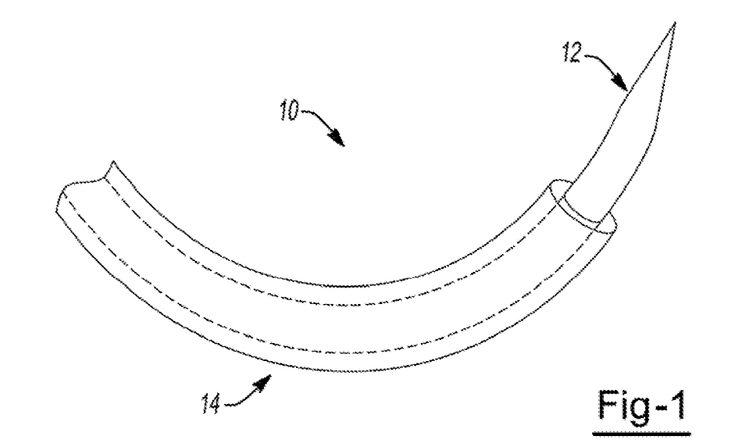
FIG. 1 illustrates a partial perspective view of a medical instrument in a catheter according to the teachings herein.

FIG. 1 illustrates a medical device 10 including a medical instrument 12, such as a needle, partially supported within a catheter 14.

Figure 2:
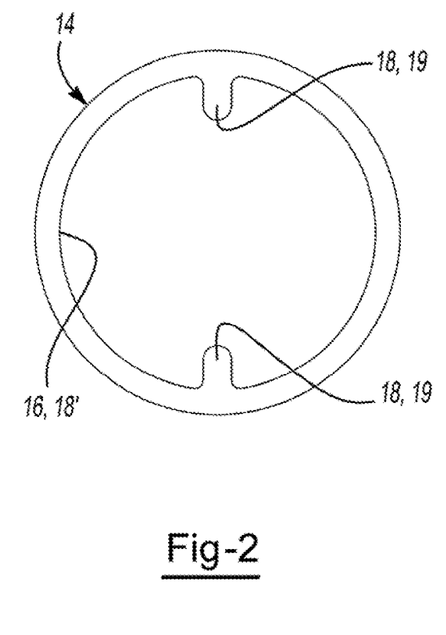
FIG. 2 illustrates a cross-sectional view of a catheter according to the teachings herein.

FIG. 2 illustrates a cross-sectional view of the catheter 14. The catheter 14 includes unlocking features 18 extending from an inner portion 16 of the catheter 14. The unlocking features 18 may be projections 19. In some embodiments, the inner portion 16 of the catheter 14 also functions as an unlocking feature 18'.

Figure 3:
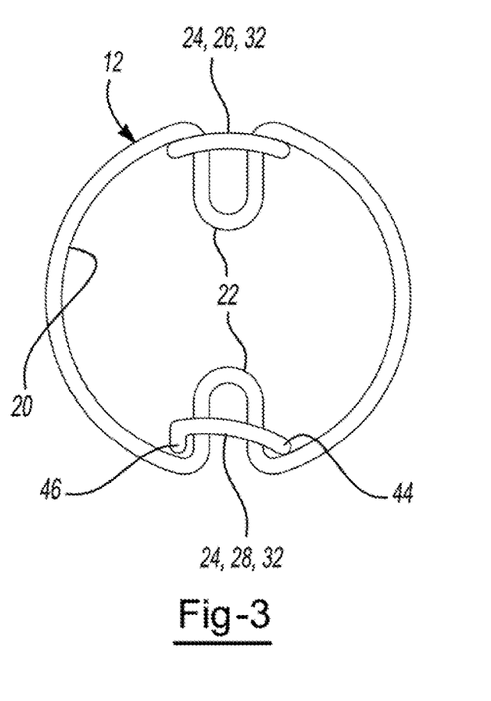
FIG. 3 illustrates a cross-sectional view of a medical instrument according to the teachings herein.

FIG. 3 illustrates a cross-sectional view of the medical instrument 12. The medical instrument 12 includes an inner portion 20, unlocking feature reliefs 22 generally conforming to the unlocking features 18 (FIG. 2), and locking features 24. In some embodiments, the locking features are one or more locking tabs 32. Each locking tab 32 has a fixed end 44 and a moveable end 46. The locking tabs 32 are moveable between a locked position 26 (upper portion of FIG. 3) and an unlocked position 28 (lower portion of FIG. 3). In the locked position 26, the moveable end 46 of the locking tab 32 is moved against the inner portion 20 of the medical instrument 12 so that the medical instrument 12 is restricting from flexing, articulating, bending, or a combination thereof. In the unlocked position 28, the moveable end 46 of the locking tab 32 is moved away from the inner portion 20 of the medical instrument 12 so that the medical instrument 12 can flex, articulate, bend, or a combination thereof. Generally, when at least a portion the medical instrument 12 is in the catheter 14, the unlocking features 18 are positioned within the unlocking feature reliefs 22. When a portion of the medical instrument 12 is in the catheter 14, the unlocking features 18 engage and move corresponding locking tabs 32 from the locked position 26 to the unlocked position 28 so that the corresponding portions of medical instrument 12 can move, bend, flex, articulate, or a combination thereof. When a portion of the medical instrument 12 is outside of the catheter 14, the corresponding locking tabs 32 are not engaged or moved by a corresponding unlocking feature 18, so the corresponding portion of the medical instrument 12 is restricted from flexing, articulating, bending, or a combination thereof (i.e., locked position 26).

Figure 4:
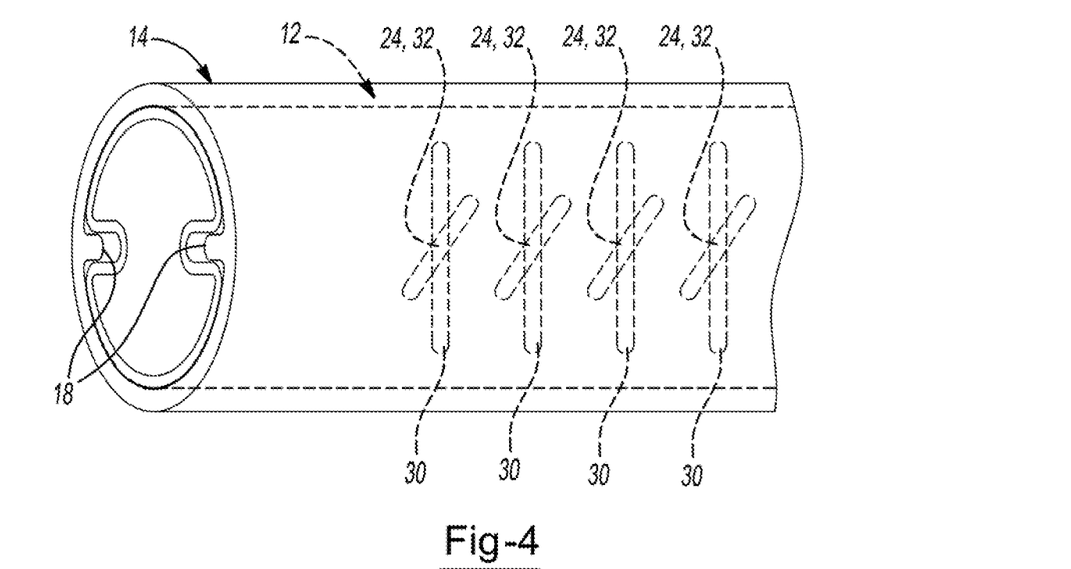
FIG. 4 illustrates a perspective view of a medical instrument in a catheter according to the teachings herein.

FIG. 4 illustrates the medical instrument 12 within the catheter 14. The medical instrument 12 includes unlocking feature reliefs 22 and locking features 24, which are locking tabs 32. The catheter 14 includes unlocking features 18. When a portion of the medical instrument 12 is in the catheter 14, the unlocking features 18 move corresponding locking features 24 or locking tab 32 from the locked position 26 to the unlocked position 28 (See bottom portion of FIG. 3).

Figure 5:
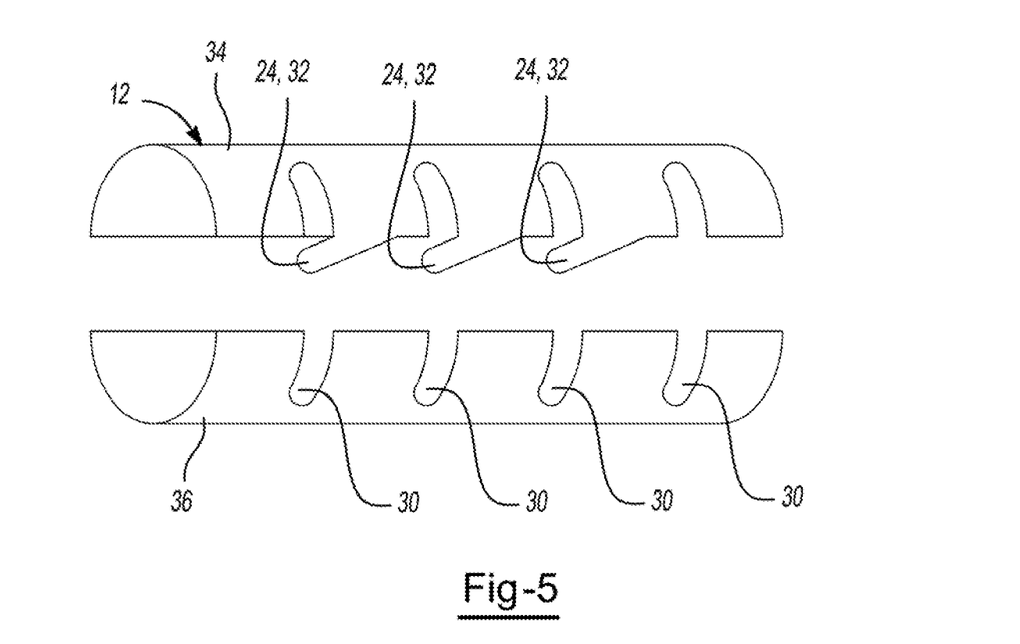
FIG. 5 illustrates a perspective view of a medical instrument according to the teachings herein.

FIG. 5 illustrates a cross-sectional view of the medical instrument 12. The medical instrument 12 includes a first portion 34 and a second portion 36. The medical instrument 12 includes locking features 24, which may be locking tabs 32 and flexibility reliefs 30.

Figure 6A:
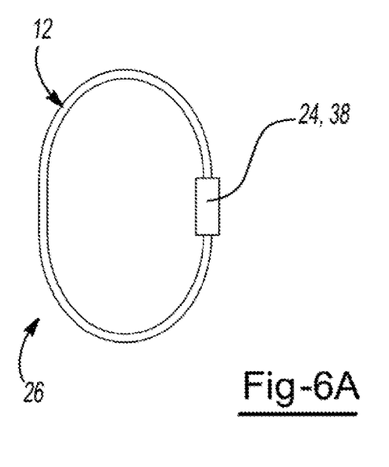
FIG. 6a illustrates a cross-sectional view of a medical instrument according to the teachings herein.
Figure 6B:
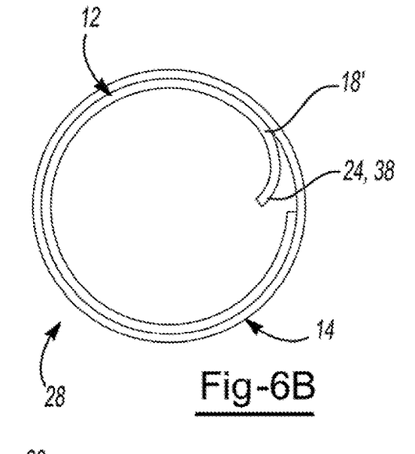
FIG. 6b illustrates a cross-sectional view of a medical instrument in a catheter according to the teachings herein.

FIGS. 6a and 6b illustrate a cross-sectional view of a medical instrument 12 (FIG. 6a) and a medical instrument 12 within a catheter 14 (FIG. 6b). The medical instrument 12 includes at least one locking feature 24, which is a hinge 38. When at least a portion of the medical instrument 12 is removed from catheter 14 (FIG. 6a), the unlocking feature 18' disengages the hinge 38 or a corresponding portion of the hinge 38 so that the medical instrument 12 is in a locked position 26. In the locked position 26, generally, the medical instrument 12 is restricted from bending articulating, flexing, or a combination thereof, and is instead generally rigid and has high column strength. In the locked position, the medical instrument 12 assumes an oval or irregular shape. Referring to FIG. 6b, when at least a portion of the medical instrument 12 is inserted into catheter 14, the unlocking feature 18' of the catheter 14 engages the hinge 38 or a corresponding portion of the hinge 38 so that the medical instrument 12 moves into an unlocked position 28. In the unlocked position 28, the corresponding portion of the medical instrument 12 assumes a circular or round shape. In the unlocked position 28, generally, the medical instrument 12 is at least partially flexible, bendable, articulable, or a combination thereof and has low column strength.

Figure 7A:
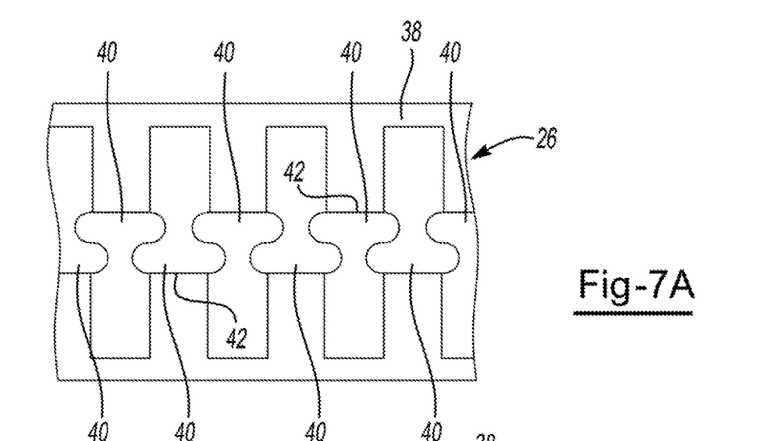
FIG. 7a illustrates a cross-sectional view of a medical instrument according to the teachings herein.
Figure 7B:
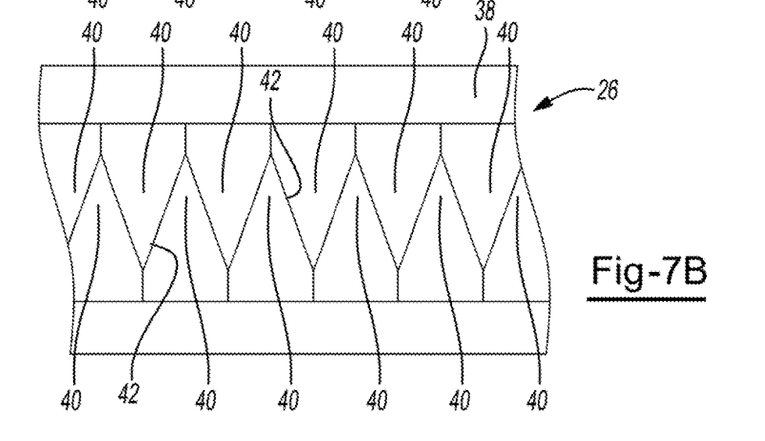
FIG. 7b illustrates a cross-sectional view of a medical instrument according to the teachings herein.

FIGS. 7a and 7b illustrate a hinge 38. The hinge 38 may include one or more interlocking extensions 40 and one or more mating interlocking recesses 42. In the locked position 26, an interlocking extension 40 engages a corresponding interlocking recess 42 so that the medical instrument 12 is restricted from flexing. In the unlocked position 28 (not illustrated), one or more of the interlocking extensions 40 and corresponding interlocking recesses 42 are disengaged separated from one another so that the medical instrument 12 can bend, flex, articulate, or a combination thereof.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

The omission in the following claims of any aspect of subject matter that is disclosed herein is not a disclaimer of such subject matter, nor should it be regarded that the inventors did not consider such subject matter to be part of the disclosed inventive subject matter.

LISTING OF REFERENCE NUMERALS 10 device
12 medical instrument
14 catheter
16 inner portion of catheter 14
18, 18' unlocking feature of catheter 14
19 projections of unlocking feature 18 of catheter 14
20 inner portion of medical instrument 12
22 unlocking feature relief of medical instrument 12
24 locking feature of medical instrument 12
26 locked position
28 unlocked position
30 flexibility reliefs of medical instrument 12
32 locking tab of medical instrument 12
34 first portion of medical instrument 12
36 second portion of medical instrument 12
38 hinge of medical instrument 12
40 interlocking extension of medical instrument 12
42 interlocking recess of medical instrument 12
44 fixed end of locking tab 32
46 moveable end of locking tab 32

The invention claimed is:

1. A device comprising:
a catheter including an inner portion and an unlocking feature; and
a medical instrument including a locking feature,
wherein when the medical instrument is located within the inner portion of the catheter, the locking feature is unlocked by the unlocking feature so that the medical instrument is configured to bend, and
wherein when the medical instrument is located outside of the catheter, the locking feature is locked so that the medical instrument is restricted from bending.

2. The device of claim 1, wherein the medical instrument includes a flexibility relief.

3. The device of claim 2, wherein the locking feature extends across the flexibility relief.

4. The device of claim 1, wherein the unlocking feature comprises a projection.

5. The device of claim 1, wherein the unlocking feature comprises two unlocking features located along opposing sides of the inner portion of the catheter.

6. The device of claim 1, wherein the locking feature includes a fixed end and a moveable end.

7. The device of claim 6, wherein the fixed end is fixed to an inner portion of the medical instrument, and the moveable end is moveable relative to the inner portion of the medical instrument.

8. The device of claim 6, wherein when the medical instrument is located within the inner portion of the catheter, the unlocking feature unlocks the locking feature by moving the moveable end.

9. The device of claim 8, wherein after the medical instrument is outside of the catheter, the moveable end resiliently moves back towards an inner portion of the medical instrument.

10. The device of claim 1, wherein the medical instrument comprises a needle.

11. The device of claim 1, wherein the medical instrument comprises an unlocking feature relief, and the unlocking feature is configured to fit within the unlocking feature relief.

12. The device of claim 11, wherein when the medical instrument is viewed is cross section, the unlocking feature relief is U-shaped.

13. The device of claim 11, wherein the locking feature extends across unlocking feature relief.

14. A method comprising:
   inserting the medical instrument into the catheter of the device of claim 1; and
   engaging the locking feature of the medical instrument with the unlocking feature of the catheter so that the medical instrument is configured to bend.

15. The method of claim 14, wherein the method includes a step of:
   moving a first portion of the medical instrument out of a distal end of the catheter so that the locking feature is disengaged by the unlocking feature so that the first portion of the medical instrument is restricted from bending, while a second portion of the medical instrument located inside of the catheter is configured to bend.

16. The method of claim 14, wherein the locking feature is a locking tab and the unlocking feature is a projection, wherein the step of engaging includes:
   engaging the locking tab with the projection.

17. A device comprising:
   a catheter including an inner portion and a projection; and
   a medical instrument including a locking tab,
   wherein when the medical instrument is located within the inner portion of the catheter, the projection engages and unlocks the locking tab so that the medical instrument is configured to bend, and
   wherein when the medical instrument is outside of the catheter, the projection is free from engaging the locking tab so that the locking tab is locked to restrict the medical instrument from bending.

18. The device of claim 17, wherein the locking tab includes a moveable end,
   wherein when the medical instrument is located within the inner portion of the catheter, the projection is configured to move the moveable end so that the medical instrument is configured to bend.

19. The device of claim 17, wherein the projection comprises two projections located along opposing sides of the inner portion of the catheter, and the locking tabs comprises two locking tabs located along opposing sides of the medical instrument.

20. The device of claim 19, wherein the medical instrument includes an unlocking feature relief that is configured to receive one of the two projections.

\* \* \* \* \*